United States Patent [19]

Schweizer

[11] 4,449,969
[45] May 22, 1984

[54] DRAINAGE RECEPTACLE WITH SUPPORT FRAME

[75] Inventor: Russell J. Schweizer, Crystal Lake, Ill.

[73] Assignee: The Kendall Company, Boston, Mass.

[21] Appl. No.: 345,504

[22] Filed: Feb. 3, 1982

[51] Int. Cl.³ .............................................. A61M 1/00
[52] U.S. Cl. ................................... 604/322; 128/760; 128/767; 248/528
[58] Field of Search .............. 248/97, 167, 528, 188.7, 248/470, 95, 144, 145; 128/760, 767, DIG. 24; 604/317, 322, 324, 326

[56] References Cited

U.S. PATENT DOCUMENTS

| | | | |
|---|---|---|---|
| 1,971,642 | 8/1934 | Champlin | 248/97 |
| 2,189,687 | 2/1940 | Thomas | 248/528 |
| 3,090,968 | 5/1963 | Buono | 604/322 |
| 3,222,019 | 12/1965 | Weisberg | 248/97 |
| 3,683,894 | 8/1972 | Villari | 128/767 |
| 4,126,135 | 11/1978 | Hinman, Jr. | 604/326 |
| 4,305,405 | 12/1981 | Meisch | 128/767 |
| 4,312,352 | 1/1982 | Meisch et al. | 604/322 |
| 4,324,244 | 4/1982 | Kurtz et al. | 604/324 |

*Primary Examiner*—C. Fred Rosenbaum
*Assistant Examiner*—J. L. Kruter
*Attorney, Agent, or Firm*—Powell L. Sprunger

[57] ABSTRACT

A drainage receptacle comprising, a container having a chamber for receiving body fluids. The receptacle has a frame having a base, a pair of spaced posts extending upwardly from the base, and a leg pivotally mounted to the base in the central portion of the leg. The leg is movable between a first inoperative position with opposed end portions of the leg located adjacent the base, and a second operative position with the opposed end portions of the leg extending outwardly from the base on opposed sides of the base. The container is secured to the frame.

4 Claims, 2 Drawing Figures

DRAINAGE RECEPTACLE WITH SUPPORT FRAME

BACKGROUND OF THE INVENTION

The present invention relates to devices for collecting body fluids.

In the past, liquid drainage devices have been proposed to collect urine from a patient. Such drainage devices may comprise a catheter which is passed through the urethra of the patient, a drainage tube connected to a proximal end of the catheter located outside the patient's body, and a collection bag connected to a downstream end of the drainage tube. In use, urine drains from the bladder through the catheter and drainage tube to the bag for collection therein. Although such devices have operated to drain urine from the patient, various devices were required to secure the drainage bag to the patient's bed, and such devices have deterred the mobility of the patient.

SUMMARY OF THE INVENTION

A principal feature of the present invention is the provision of an improved receptacle for collecting body fluids.

The receptacle of the present invention comprises, a container having a chamber for receiving body fluids. The receptacle has a frame having a base, a pair of spaced posts extending upwardly from the base, and a leg pivotally mounted to the base in a central portion of the leg. The leg is movable between a first position with opposed end portions of the leg located adjacent the base, and a second position with the opposed end portions of the leg extending outwardly from the base on opposed sides of the base. The receptacle has means for securing the container on the frame.

A feature of the present invention is that the receptacle has a cord secured to the frame for supporting the receptacle from a support structure, such as a bed rail, with the leg located in the first inoperative position.

Another feature of the present invention is that the leg may be moved to the second operative position, and the container may be supported by the frame on the floor.

Yet another feature of the invention is that the receptacle permits the patient to move about with the leg located in the second position, since the receptacle is not secured to the supporting structure.

Further features will become more fully apparent in the following description of the embodiments of this invention and from the appended claims.

DESCRIPTION OF THE PREFERRED EMBODIMENTS

Figure 1:
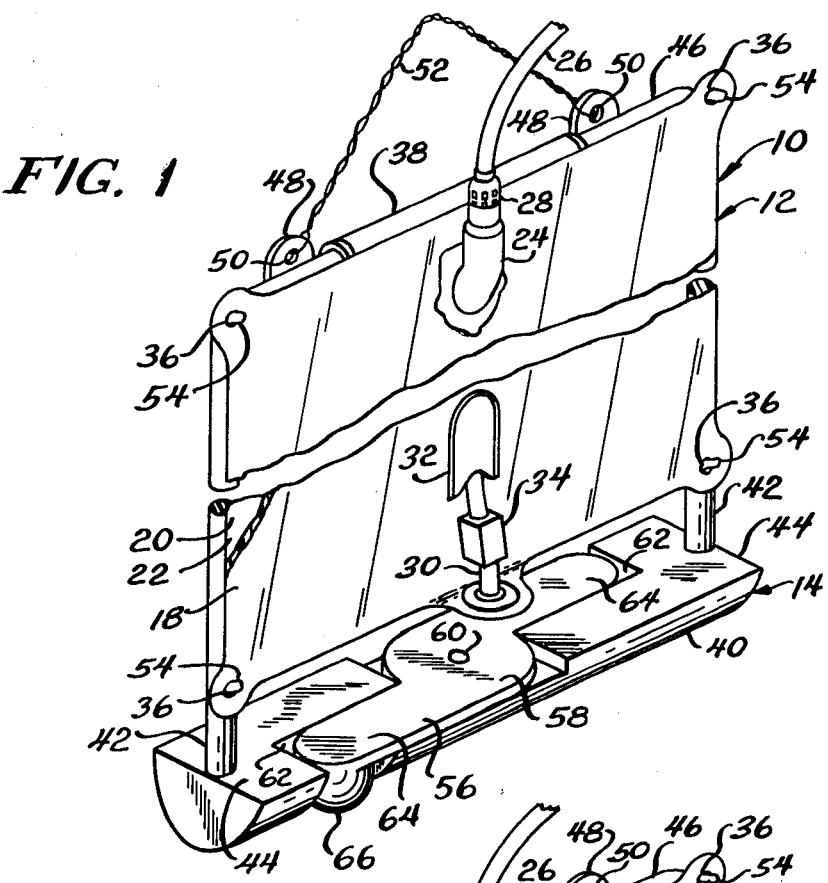
FIG. 1 is a fragmentary perspective view of a drainage receptacle of the present invention with a leg of the receptacle being located in an inoperative position.
Figure 2:
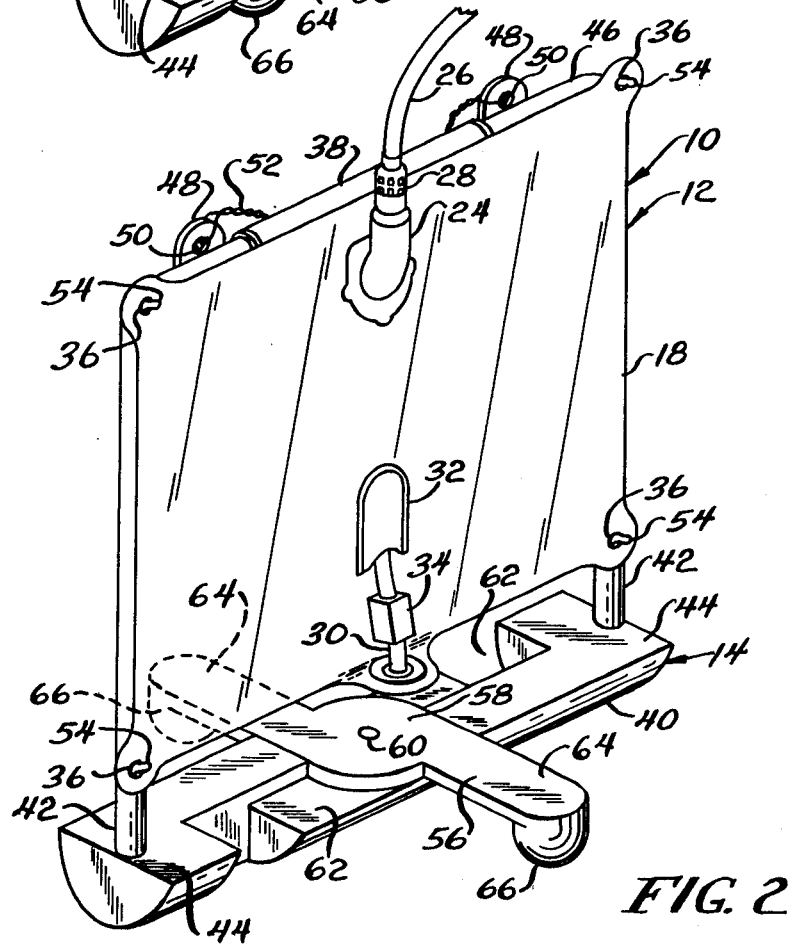
FIG. 2 is a perspective view of the drainage receptacle with the leg moved to an operative position.

Referring now to FIGS. 1 and 2, there is shown a drainage receptacle generally designated 10 comprising a container 12 and a frame 14. The container 12 has a front wall 18 of flexible plastic material, and a back wall 20 of flexible plastic material, with the walls 18 and 20 being joined at their periphery by suitable means, such as heat sealing, in order to define a chamber 22 between the front and back walls 18 and 20. The container 12 has a hollow connector 24 comprising a drip chamber attached to an upper portion of the front wall 18 with the connector 24 communicating with the chamber 22. The receptacle 10 has a drainage tube 26 with a downstream end received in the connector 24 such that a lumen in the drainage tube 26 communicates with the connector 24. As shown, the connector 24 may have a suitable vent 28 comprising openings in the connector 24 and a bacteria filter of known type to filter bacteria from the air passing from the atmosphere into the connector 24 and chamber 22.

The container 12 has a tubular section 30 attached to a lower portion of the front wall 18 with the tubular section 30 communicating with the chamber 22. The container 12 has a pocket 32 on the front wall 18 to receive an outer end of the tubular section 30 in a storage position of the tubular section 30. The tubular section 30 has a clamp 34 of suitable type in order to releasably close the tubular section 30. In use, the tubular section 30 is removed from the pocket 32 and the clamp 34 is released in order to drain urine from the container chamber 22, after which the clamp 34 is again closed and the outer end of the tubular section 30 is inserted into the pocket 32 in order to retain the tubular section 30 in the storage position. The container 12 has a plurality of apertures 36 extending through the walls 18 and 20 adjacent the four corners of the container 12. The container 12 also has a flap 38 extending from an upper portion of the container 12.

The frame 14 has an elongated base 40 with an arcuate lower surface. The frame 14 has a pair of spaced posts 42 extending upwardly from opposed end portions 44 of the base 40, with the posts 42 being located adjacent opposed sides of the container 12. The frame 14 has an upper bar 46 extending between upper ends of the posts 42 at a location adjacent an upper portion of the container 12. As shown, the upper bar 46 has spaced upstanding ears 48 with openings 50 to receive opposed end portions of a cord 52. The frame 14 also has a plurality of spaced bosses 54 located to be received in the apertures 36 of the container 12 in order to releasably secure the container 12 to the frame 14 with the bosses 54 received in the apertures 36. Also, the flap 38 of the container 12 may be wrapped about the upper bar 46 and secured in place.

As can be seen in FIG. 1, the frame 14 including base 40, posts 42,42 and upper bar 46 form a generally rectangular, substantially uniplanar frame.

The frame 14 has an elongated leg 56 with a central portion 58 of the leg 56 being pivotally mounted to a central portion of the base 40 by a pin 60. Leg 56 has an overall length less than that of base 40, as is shown in FIGS. 1 and 2. The base 40 has a pair of recesses 62 to receive opposed end portions 64 of the leg 56 in a first inoperative position of the leg 56, as shown in FIG. 1, with the opposed end portions 64 of the leg 56 being located adjacent the base 40. As shown in FIG. 2, the leg 56 may be moved to a second operative position with the opposed end portions 64 of the leg 56 extending from opposed sides of the base 40. In a preferred form, the leg 56 extends approximately perpendicularly to the base 40 at the second position. The leg 56 has lower protuberances 66 extending downwardly from the opposed ends of the leg 56.

Thus, in accordance with the present invention, the leg 56 may be moved to the first inoperative position, as shown in FIG. 1, and the receptacle 10 may be supported by the cord 52 from a suitable support structure, such as a bed rail. Alternatively, the leg 56 may be moved to the second operative position, as shown in FIG. 2, and the receptacle 10 may be placed on the floor with the protuberances 66 contacting the floor along with the lower surface of the base 40, in order to support the container 12 in an upright position on the floor. In this configuration, the patient is free to move about while carrying the receptacle 10. Also, the container 12 may be removed from the frame 14 by removing the bosses 54 from the apertures 36, and the flap 38 from the frame 14.

The foregoing detailed description is given for clearness of understanding only, and no unnecessary limitations should be understood therefrom, as modifications will be obvious to those skilled in the art.

I claim:

1. A drainage receptacle and frame combination comprising:
   a flat, generally rectangular container means having a pair of opposed flexible walls defining a chamber for receiving body fluids, and aperture means formed through the walls of said container at the four corners thereof;
   a generally rectangular, substantially uniplanar frame means having a base, a pair of spaced, generally vertically oriented and parallel posts fixed to and extending upwardly from the base, each of said posts including an upper and a lower boss means for receiving respectively, upper and lower apertures of said rectangular container to fixedly mount said container means on said frame means, said base having a leg pivotally mounted centrally of the base, said leg having opposed end portions, said leg having an overall length less than that of said base and being movable from a first inoperative position with said opposed end portions of the leg located adjacent the base, generally parallel thereto, and a second operative position with opposed end portions of the leg extending outwardly from the base, at substantially right angles thereto, said leg being free of connection to the container;
   an elongated cord means on the frame for supporting the container and frame; and
   means for securing spaced portions of the cord to the frame;
   whereby, in use, said frame means and container means combination may be selectively supported either by said cord means, from a suitable support structure such as a bed rail, or by said base with said leg extended to said second operative position, by placing said base on a horizontal support surface such as a floor.

2. The receptacle of claim 1 wherein said base includes a pair of recesses to receive the end portions of the leg in said first position.

3. The container means of claim 1 wherein said opposed end portions of the leg have downwardly extending protuberances.

4. The receptacle of claim 1 wherein said frame means includes an upper bar extending between the upper ends of the posts, said means for securing spaced portions of the cord to the frame means being mounted on said upper bar.

* * * * *